(12) United States Patent
Greenhut

(10) Patent No.: US 6,454,719 B1
(45) Date of Patent: Sep. 24, 2002

(54) APPARATUS AND METHOD FOR DIAGNOSIS OF CARDIAC DISEASE USING A RESPIRATION MONITOR

(75) Inventor: Saul E. Greenhut, Aurora, CO (US)

(73) Assignee: Pacesetter, Inc., Sylmar, CA (US)

( * ) Notice: Subject to any disclaimer, the term of this patent is extended or adjusted under 35 U.S.C. 154(b) by 1 day.

(21) Appl. No.: 09/630,298

(22) Filed: Aug. 1, 2000

(51) Int. Cl.[7] ................................................ A61B 5/08
(52) U.S. Cl. ...................... 600/484; 600/481; 600/529; 600/547
(58) Field of Search ................................. 600/529, 484, 600/547, 481; 607/17, 19, 20

(56) References Cited

U.S. PATENT DOCUMENTS

| | | | |
|---|---|---|---|
| 5,207,219 A | 5/1993 | Adams et al. | |
| 5,271,395 A | * 12/1993 | Wahlstrand et al. | 600/547 |
| 5,300,093 A | * 4/1994 | Koestner et al. | 607/32 |
| 5,438,983 A | * 8/1995 | Falcone | 607/27 |
| 5,441,523 A | 8/1995 | Nappholz | |
| 5,562,712 A | 10/1996 | Steinhaus et al. | |
| 5,713,937 A | 2/1998 | Nappholz et al. | |
| 5,720,770 A | 2/1998 | Nappholz et al. | |
| 5,824,020 A | 10/1998 | Cooper | |
| 5,876,353 A | * 3/1999 | Riff | 600/547 |
| 5,935,081 A | * 8/1999 | Kadhiresan | 600/513 |
| 5,957,861 A | * 9/1999 | Combs et al. | 600/547 |
| 6,275,727 B1 | * 8/2001 | Hopper et al. | 600/513 |
| 6,336,903 B1 | * 1/2002 | Bardy | 600/508 |

* cited by examiner

Primary Examiner—Robert L. Nasser
Assistant Examiner—Patricia Mallari
(74) Attorney, Agent, or Firm—Gottlieb, Rackman & Reisman, P.C.

(57) ABSTRACT

The cardiac condition of a patient is determined by a cardiac monitor apparatus using a respiration parameter such as a current respiration signal or a respiration rate. The variability of the respiration parameter is used to generate a signal indicative of the current heart failure status of the patient, and more particularly whether the patient's condition has improved, worsened, or remained unchanged over a predetermined time period. The circuitry for detecting the respiration parameter may be implanted in the patient, for example as part of a pacemaker, while at least some of the analyzing circuitry may be external and remote from the patient. Alternatively the whole device may be implantable.

33 Claims, 17 Drawing Sheets

CHF

NORMAL

APPARATUS AND METHOD FOR DIAGNOSIS OF CARDIAC DISEASE USING A RESPIRATION MONITOR

BACKGROUND OF THE INVENTION

A. Field of the Invention

This invention pertains to a novel apparatus and method for diagnosing the heart condition of a patient by monitoring his pulmonary function.

B. Description of the Prior Art

Studies have demonstrated heart failures are related to one or more of the following conditions: coronary artery disease, valvular heart disease, heart muscle disease, hypertension, pericardial disease, congenital heart disease, infection, tachyarrhythmia, and cardiac tumors.

Fundamentally, aerobic exercise training may decrease the symptoms associated with congestive heart failure (CHF) and increase heart rate variability (HRV), indicating an improved autonomic responsiveness and improving a patient's exercise tolerance and quality of life. Current standard techniques for treating heart failure typically include angiotensin converting enzyme (ACE) inhibitors, diuretics, and digitalis. The main function of ACE inhibitors is to act as vasodilators, to reduce arterial blood pressure and reduce pulmonary capillary wedge pressure. ACE inhibitors have also been shown to increase cardiac output and increase the capability of heart failure patients to exercise. Diuretics decrease body fluid and hence reduce the cardiac load. Digitalis has been shown to increase the inotropic action of the heart and increase cardiac output in heart failure patients.

Ultimately, heart transplants and other cardiac surgeries are also alternative therapies, but only for a small percentage of patients with particular etiologies.

The New York Heart Association has developed a heart condition classification expressed as Stages I, II, III, and IV, determined as a combination of symptoms exhibited by a patient, including the ability to breathe properly, exercise or perform normal physical activities . Stage I is characterized by no breathlessness with normal physical activity. Stage II is characterized by breathlessness associated with normal physical activity. Stage III is characterized by breathlessness associated with even minimal physical activity. Stage IV is characterized by breathlessness even while a patient is at rest.

Several methods for monitoring the progression and severity of CHF are known. One powerful non-invasive method of stratifying mortality comprises measuring the HRV. It is not, however, an effective means of predicting CHF and, specifically, cannot be used in patients having sick sinus syndrome.

Another method of tracking the progression of CHF includes measurement of the ejection infraction using echocardiography or catheterization. The ejection infraction is a measure of the cardiac systolic function and can be used as a predictor of mortality. The ejection infraction, however, currently cannot be measured conveniently, or continuously, in an ambulatory patient.

OBJECTIVES AND SUMMARY OF THE INVENTION

It is an objective of the present invention to provide a system for determining a patient's breathing pattern and then to use this pattern to indicate a patient's cardiac condition.

A further objective is to provide a cardiac treatment system which monitors a patient's cardiac condition over a predetermined time period and, based on his breathing pattern, indicates whether the patient's condition has improved, worsened or remaining unchanged.

A further objective is to provide a reliable technique for monitoring and tracking the severity of CHF in an ambulatory patient through the variability in his respiration rate and pattern.

Other objectives and advantages of the invention will become apparent from the following description of the invention.

CHF patients typically have a characteristic breathing pattern which is dominated by a low-frequency variation as compared to healthy persons. More specifically, CHF patients have a periodic breathing pattern characterized by sequential deep and shallow breaths (FIGS. 8B and 8C) as compared to the breathing pattern of a healthy person (FIGS. 9B and 9C). As illustrated in the figures, healthy persons have a regular breathing pattern with a peak frequency greater than 0.15 Hz. On the other hand, CHF patients tend to have an abnormal breathing pattern with a low frequency dominant signal (less than 0.03 Hz) resembling Cheyne-Stokes respiration, characterized by periods of respiration followed by periods of non-breathing. Abnormal breathing patterns may result in a gas exchange deficiency, autonomic nervous system disruption and/or other problems. FIGS. 8A–8C and 9A–9C further illustrate a correlation in both the time and the frequency domains between the heart rate of a person and his respiration rate.

The automatic respiration mechanism, which is governed by the central nervous system and other peripheral functions, controls the respiration and heart rates, as well as the sympathetic and the parasympathetic cardiac efferent neurons. Conversely, the performance of the autonomic nervous system as well as the patient's cardiac system can be derived from the variability of the respiration rate.

The present invention contemplates monitoring and recording the variability of respiration patterns for a cardiac patient. A respiration parameter (the respiration rate, tidal volume, low frequency power, high-frequency power, or ratio of the latter two) is first determined using an implanted device such as a defibrillator, a pacemaker or other event monitor. Currently, as these devices do not have sufficient calculating power to make the trend calculations necessary to determine respiration variability, the respiration parameter may be transmitted to an external device for processing. It is anticipated that future implantable devices will have sufficient calculating power to determine the respiration variability. The respiration parameter is then measured using the electrogram sensing interval or internal or external thoracic impedance. This respiration parameter is used to calculate the respiration variability and to indicate cardiac condition.

Continuously tracking respiration variability and breathing patterns of cardiac patients is beneficial for many other reasons as well. First, a clinician may track the progression or reversion of cardiac disease. Second, as certain landmarks are reached, the clinician could administer treatment or change therapies proactively. Third, the respiration variability provides a physician with an indication of how well a recovering cardiac patient is responding to a prescribed rehabilitation program.

DETAILED DESCRIPTION OF THE INVENTION

Figure 1:
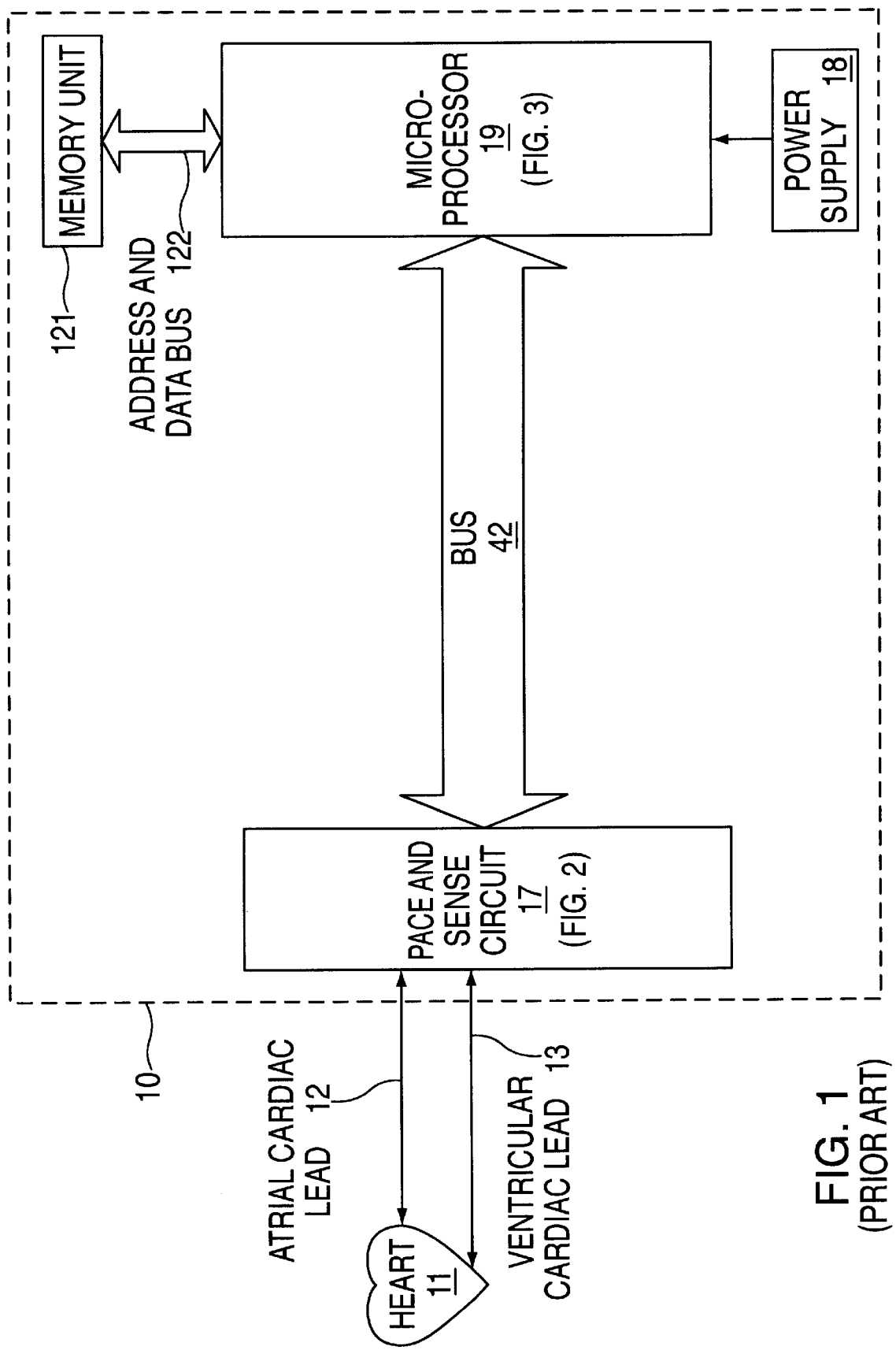
FIG. 1 shows a block diagram of a pacemaker constructed in accordance with this invention.

Details of a pacemaker which can perform the functions described above are now described in conjunction with FIGS. 1–6. FIG. 1 shows a block diagram of the pacemaker 10. The pacemaker 10 is designed to be implanted in a patient and is connected by leads 12 and 13 to a patient's heart 11 for sensing and pacing the heart 11 as described, for example, in U.S. Pat. No. 5,441,523 by T. Nappholz, entitled FORCED ATRIOVENTRICULAR SYNCHRONY DUAL CHAMBER PACEMAKER, and incorporated herein by reference. Briefly, the atrial cardiac lead 12 extends into the atrium of the heart 11 and the ventricular cardiac lead 13 extends into the ventricle of the heart 11. Leads 12 and 13 terminate in electrodes which are used both for sensing electrical activity in the heart and applying pacing pulses to the heart. The pacemaker 10 includes a pace and sense circuit 17 for detecting analog signals from leads 12 and 13 and for delivering pacing pulses to the heart 11; a microprocessor 19 which, in response to numerous inputs received from the pace and sense circuit 17, generates different control and data outputs to the pace and sense circuit 17; and a power supply 18 which provides a voltage supply to the pace and sense circuit 17 and the microprocessor 19 by electrical conductors (not shown). The microprocessor 19 is connected to a memory unit 121 by an address and data bus 122. The microprocessor 19 and the pace and sense circuit 17 are connected to each other by a number of data and control lines collectively shown in FIG. 1 as bus 42.

Figure 2:
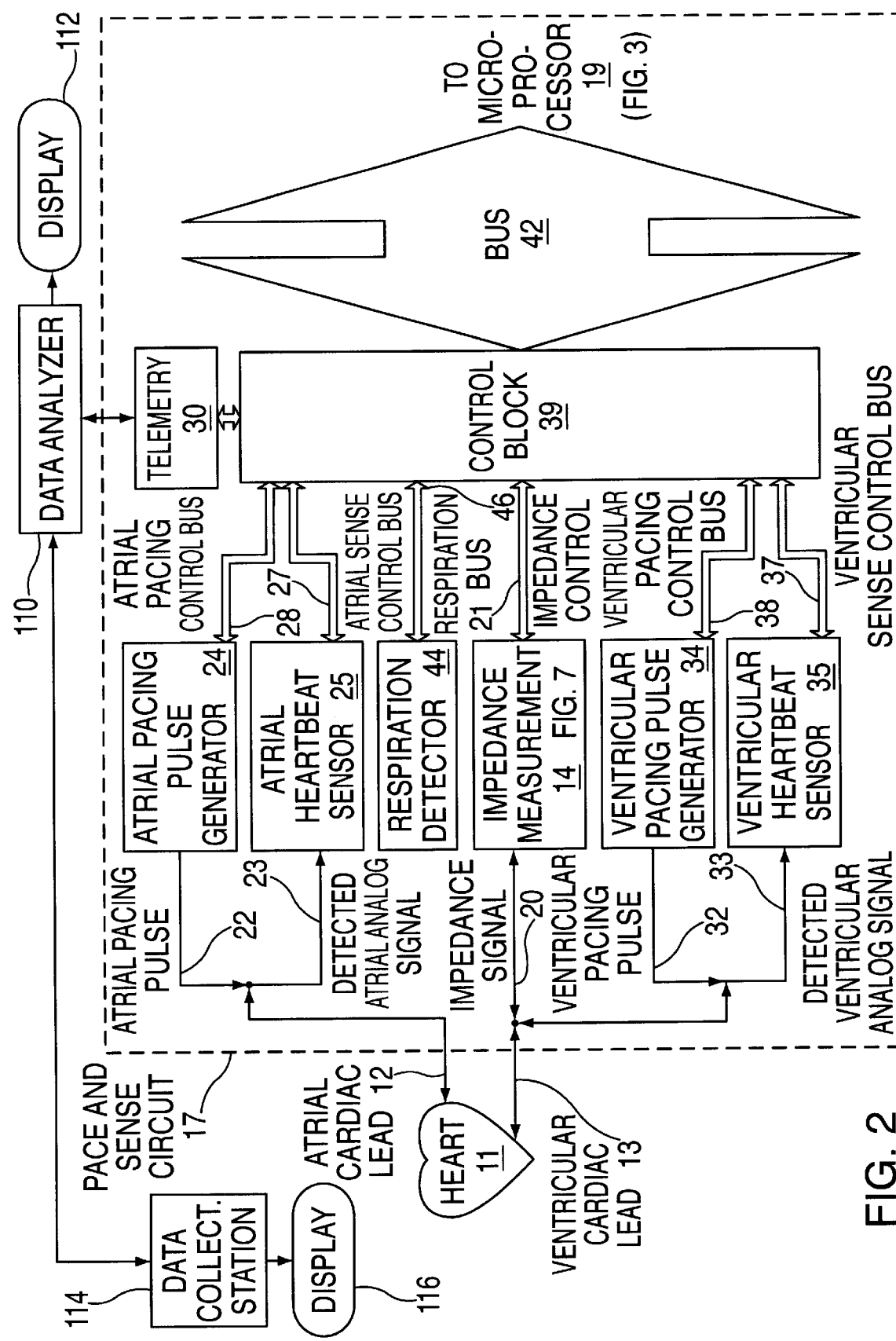
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19. In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22. Similarly, the ventricular pacing pulse generator 34 receives from the control block 39, via a ventricular pacing control bus 38, a ventricular pace control signal and a ventricular pacing energy control signal to generate a ventricular pacing pulse 32. The atrial and ventricular pace control signals determine the timings of atrial and ventricular pacing, while the atrial and ventricular pacing energy control inputs determine the magnitudes of the respective pulses.

To effectuate an impedance measurement, the microprocessor 19 sends a signal on the impedance control bus 21 to activate the impedance measurement circuit 14. The impedance measurement circuit 14 then applies a current to the ventricular cardiac lead 13 via lead 20 and measures the voltage resulting from the applied current, as discussed in more detail below. These current and voltage signals define an impedance that is representative of the patient's metabolic demand, and more particularly, of the instantaneous minute volume. This instantaneous minute volume is then filtered and further modified by subtracting from it a long term average value. The resulting parameter is the minute volume parameter.

The pace and sense circuit 17 further includes a respiration detector 44 which detects the respiration function of the patient. This information is transmitted to the control block 39 via respiration bus 46. In the preferred embodiment of the invention, the respiration function is determined from the impedance measurements taken by impedance measurement circuit 14 as discussed in detail below. If the metabolic demand is determined by other means, then the respiration detector 44 may use other signals to detect respiration.

The telemetry circuit 30 provides a bidirectional link between the control block 39 of the pace and sense circuit 17 and an external device such as a programmer (not shown). It allows data such as the operating parameters to be read from or altered in the implanted pacemaker. In addition, the telemetry circuit 30 is also used to send data to a data analyzer 110. In accordance with this invention, the data analyzer 110 receives data indicative of the cardiac condition of the patient, as discussed below in conjunction with FIGS. 4–7B. The data analyzer 110 is adapted to provide to a clinician information about the patient. This information is shown in a display 112. The data analyzer 110 may also communicate with a data collection station 114. Data collection station 114 has its own display 116 on which information about one or more patients may be shown automatically, or on demand.

Figure 3:
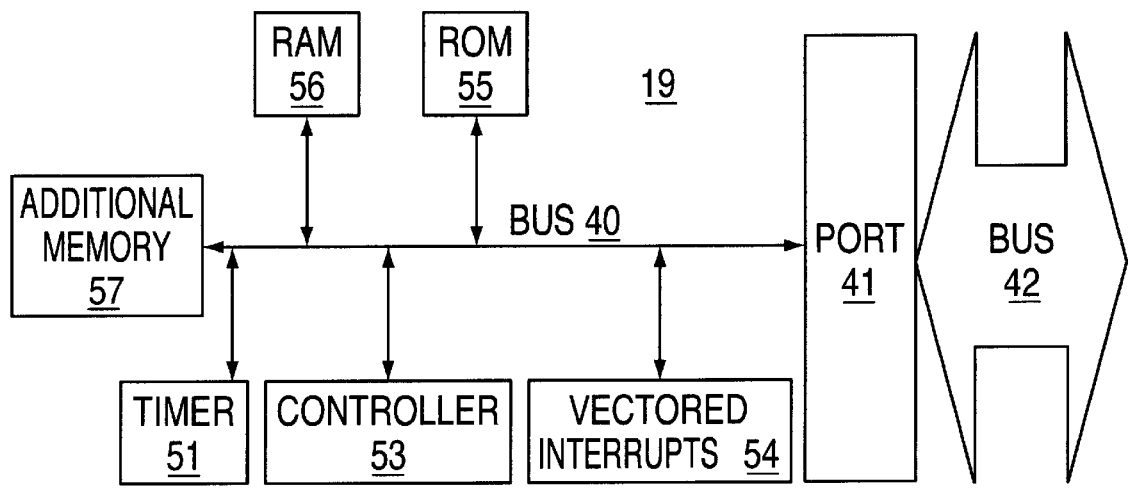
FIG. 3 shows a block diagram of a microprocessor for the pacemaker of FIG. 1.

FIG. 3 shows the microprocessor 19 having a timer circuit 51 for generating several timing signals, a controller 53, a vectored interrupts circuit 54, a ROM 55, a RAM 56, an additional memory 57, and an interface port 41. Signals between these elements are exchanged via an internal communications bus 40. The timer circuit 51 generates various timing signals. The timer circuit 51 and its associated control software implement some timing functions required by the microprocessor 19 without resorting entirely to software, thus reducing computational loads on, and power dissipation by, the controller 53.

The RAM 56 acts as a scratchpad and active memory during the execution of the programs stored in the ROM 55 and used by the microprocessor 19. ROM 55 is used to store programs including system supervisory programs, detection algorithms for detecting and confirming arrhythmias, programs for determining the rate of the pacer and programs for storing data in additional memory 57. This data pertains to the functioning of the pacemaker 10 and the electrogram provided by the cardiac leads 12 and 13.

The microprocessor 19, through its port 41, receives status and/or control inputs from the pace and sense circuit 17, including the sense signals from the sensors 25, 35 (FIG. 2). Using controller 53, it performs various operations including arrhythmia detection. The microprocessor 19 also produces outputs, such as the atrial and ventricular pacing control which determine the type of pacing that is to take place. Controller 53 adjusts the rate of the atrial and/or ventricular pacing to conform to the metabolic demand of the patient as set forth below.

Figure 4:
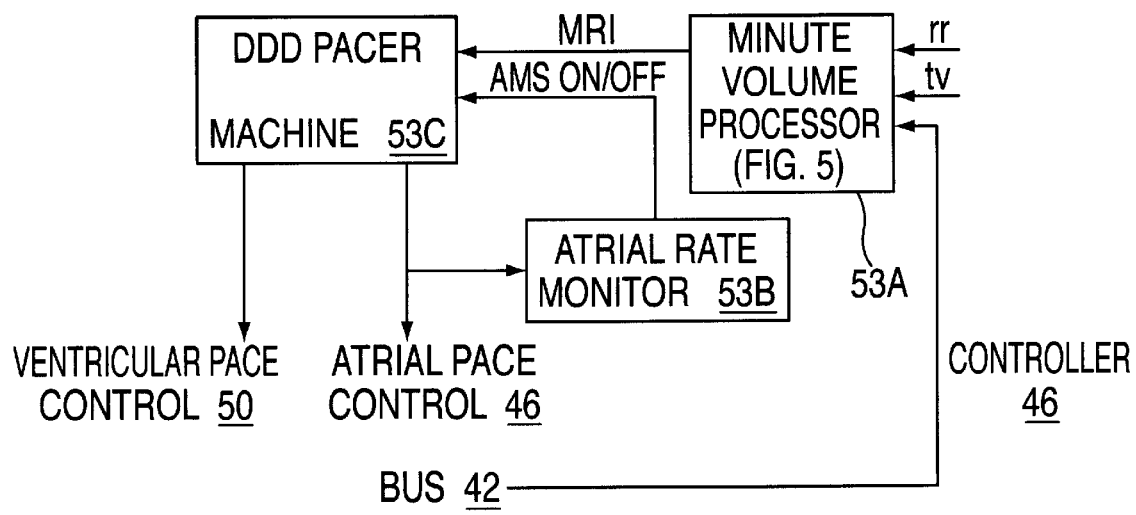
FIG. 4 shows details of the controller for the microprocessor of FIG. 3.

FIG. 4 shows the block diagram of the controller 53 of FIG. 3. The controller 53 includes a DDD pacer 53C, which is preferably a state machine, a minute volume processor 53A and an atrial rate monitor 53B. The minute volume processor 53A uses the transthoracic impedance signal ti and the respiration rate rr to generate a Metabolic Rate Interval (MRI). Details of how the transthoracic impedance signal ti and the respiration rate rr are derived are discussed below. The pacer 53C uses MRI to determine the length of each interval in the timing cycle. While the pacemaker 10 preferably operates in a DDD mode, it should be understood that it can operate in other modes as well. The atrial rate monitor 53B generates an automatic mode switching (AMS) signal upon detection of a non-physiological atrial rate and rhythm. This AMS signal automatically switches the pacemaker 10 to a pacing mode in which atrial senses do not trigger ventricular pacing pulses. When a physiological atrial rate resumes, the AMS signal is deactivated and the pacemaker returns to an atrial tracking mode.

Figure 5:
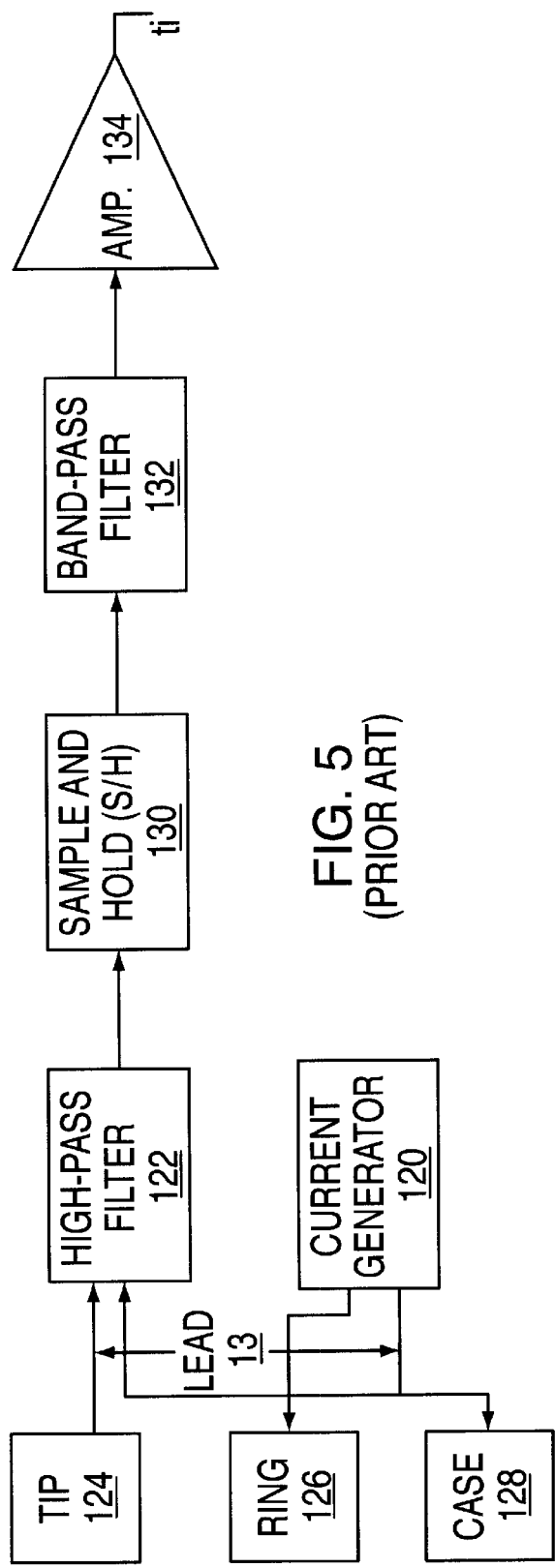
FIG. 5 shows a block diagram for a prior art circuit used to determine the thoracic impedance.

A patient's respiration rate (rr) and transthoracic impedance (ti) may be detected using various methods. For example, a known impedance measurement circuit (disclosed in U.S. Pat. No. 5,824,020, incorporated herein by reference) is depicted in FIG. 5 and includes a current generator 120 and a high pass filter 122 coupled to one of the patient leads, such as lead 13. Other leads may be used as well for measuring impedance as described, for example, in U.S. Pat. No. 5,562,712.

The lead 13 includes a tip electrode 124 and a ring electrode 126. As known in the art, at predetermined times, the current generator 120 applies current pulses between the ring electrode 126 and pacemaker case 128. The corresponding voltage is sensed between the tip electrode 124 and case 128. Typically, each current pulse has a pulse width of about 7.5 $\mu$sec, at a repetition rate of about 18 pulses per second and an amplitude of about 1 mA. This pulse repetition rate is chosen at well above twice the Nyquist sampling rate for the highest expected intrinsic heart beats. Moreover the pulse repetition rate is also chosen so that it can be easily differentiated from noise induced by a power line at 50 or 60 Hz.

The signal sensed at tip 124 is passed through the high pass filter 122 selected to accept the 7.5 $\mu$sec pulses and exclude all noise signals. After filtering, the voltage signal is sampled by a sample and hold (S/H) circuit 130. Preferably the S/H circuit 130 takes samples before the start of the test pulses from current generator 120 (to enhance the effectiveness of the filter 122) and at the end of the pulse duration. The output of S/H circuit 130 is passed through a band-pass filter 132 which selects the signals in the range of normal respiration rates, typically 5–60 cycles/minute. The output of the band-pass filter 132 is amplified by amplifier 134 to generate a transthoracic impedance signal ti.

Figure 6:
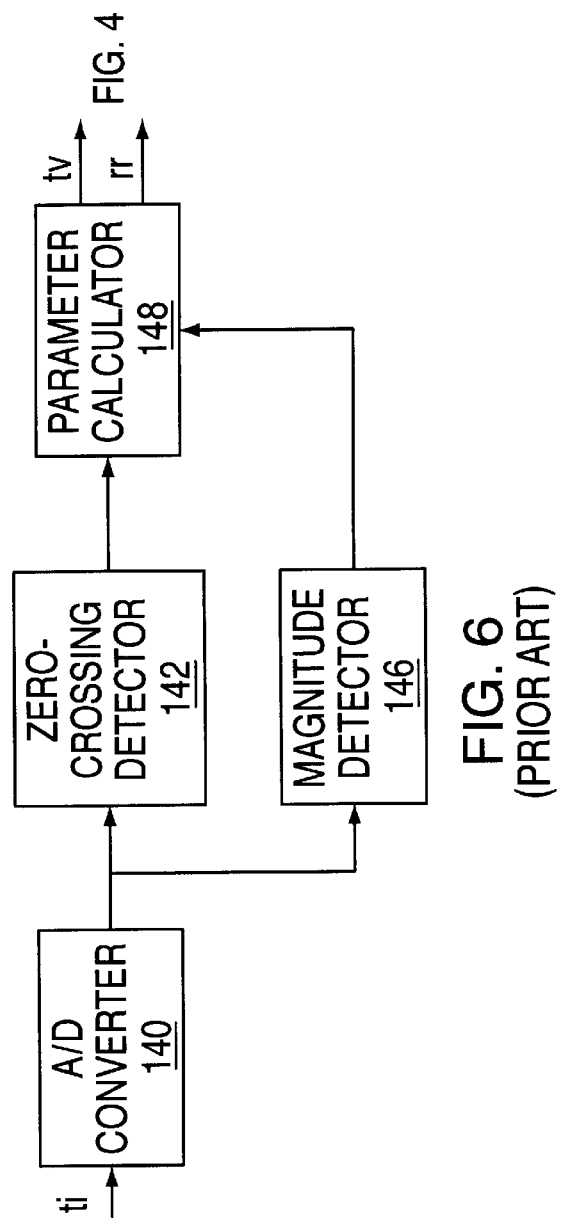
FIG. 6 shows a block diagram for a prior art circuit for converting the thoracic impedance to a respiration rate and other parameters.

Referring to FIG. 6, the signal ti is processed further using an A/D converter 140, a zero crossing detector 142, a magnitude detector circuit 146 and a parameter calculator circuit 148. Circuits 140 and 142 are preferably discrete hardware components. The remaining circuits 146 and 148 are implemented by a microprocessor. For the sake of clarity, circuits 146 and 148 are shown here as discrete circuits.

The transthoracic impedance signal ti is first fed to the A/D converter 140 to generate a digital representation of the signal ti. The output of the A/D converter is fed to the zero crossing detector 142 which generates a zero crossing signal whenever it detects a change of sign in signal ti.

The magnitude of the signal ti is determined by magnitude detector circuit 146.

The outputs of circuits 142 and 146 are fed to the parameter calculator circuit 148 as shown. At regular intervals, the parameter calculator circuit 148 calculates several parameters, including the respiration rate (rr) and the tidal volume (tv). Details of the calculations used to determine these parameters are disclosed in commonly assigned U.S. Pat. No. 5,824,020, incorporated herein by reference. These two parameters rr and tv are provided to the minute volume processor 53A of FIG. 4.

Figure 7A:
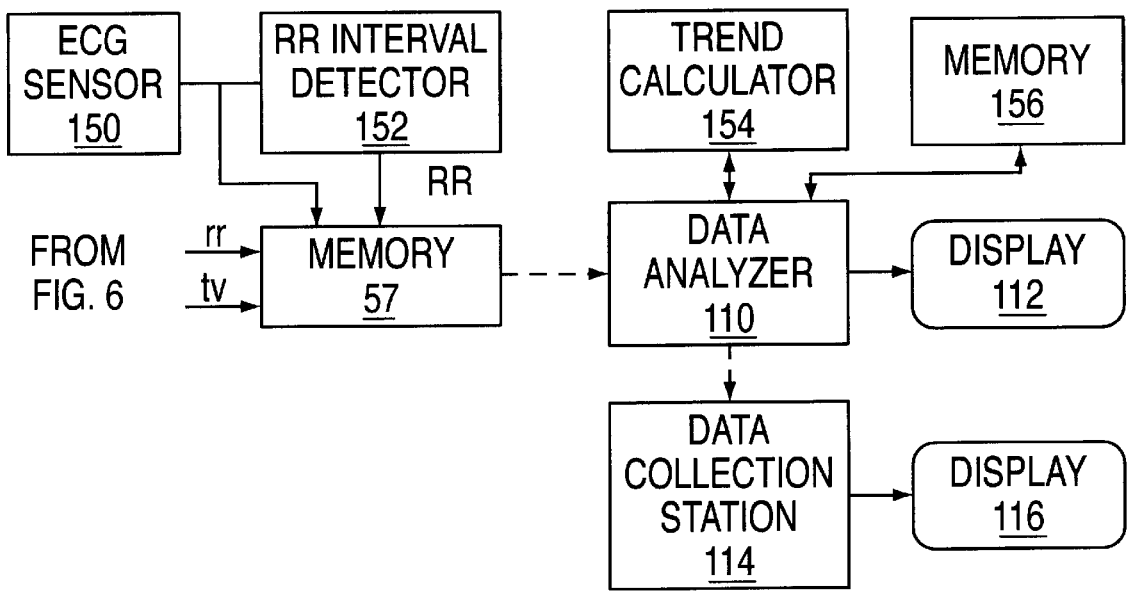
FIGS. 7A and 7B show block diagrams of the circuit elements for determining respiration variability internally and externally of an implantable pacemaker, respectively.

Referring now to FIG. 7A, the pacemaker 10 is also provided with an ECG sensor 150 which may be implemented in a number of ways, well known in the art, and used to digitally detect the ECG of the patient. This ECG is provided to an RR interval detector 152 adapted to detect the current R-wave to R-wave interval (RR) of the patient.

Values for the RR interval, the ECG, and parameters rr and tv are derived by the parameter calculator 148 in FIG. 6 and are stored at predetermined intervals in a memory, such as the additional memory 57. For example, the values of each of these parameters may be stored for a period of three minutes every hour. In one embodiment of the invention shown in FIG. 7A, at the end of the three-minute period (or at any other time prior to the next three-minute period) the data stored in additional memory 57 is downloaded to data analyzer 110. As described above, in conjunction with FIG. 2, external data analyzer 110 is provided with a display 112, and can communicate with a remote station 114 with its own display 116. In addition, the data analyzer 110 is also associated with a trend calculator 154.

The data received from the pacemaker 10 is stored by trend calculator 154 in a memory 156. The trend calculator 154 uses this data to calculate a trend in the respective parameters and in the corresponding condition of the patient as reflected by the variations in these parameters. The calculations are provided to the data analyzer 110. The data analyzer 110 uses these calculations to generate information for a clinician about the patient, which information is shown on display 112 and/or transmitted to station 114.

If the patient is ambulatory, the data analyzer 110, trend calculator 154 memory 156 and display 112 may be housed in a common case which may be a holster-type device carried by the patient at all times. Otherwise, these elements may be incorporated into an external stationary device disposed at the patient's bedside. The data can then be analyzed by the external device and sent to the data collection station as described in U.S. Pat. Nos. 5,713,937 and 5,720,770.

Figure 7B:
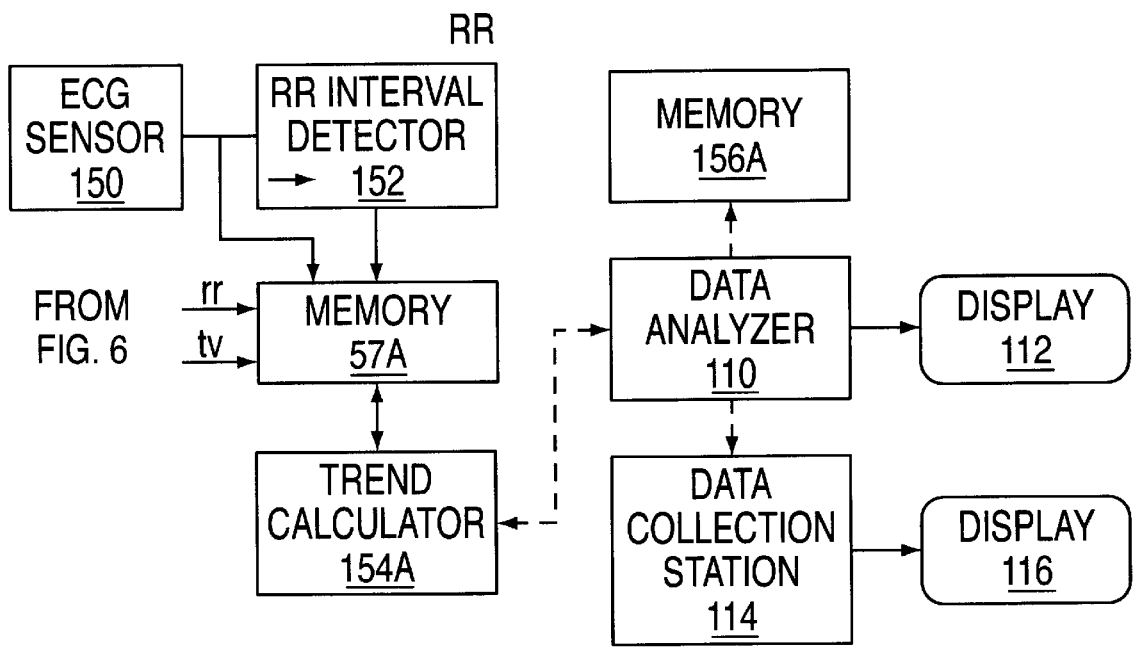

Data from the pacemaker 10 is downloaded and stored in memory 156 because present pacemakers may not contain sufficient memory and/or computational power to perform the trend analysis required for the diagnosis envisioned by the present invention. However, it is expected that in the near future, implanted devices will have sufficient data storage to store all these data and even perform at least part of the trend analysis. In this latter case, as shown in FIG. 7B, all the data required for the computations is stored in the memory 57A and the trend calculator 154A may be incorporated into the pacemaker 10. The results of the calculations performed by the trend calculator 154A are then transmitted to the data analyzer 110. The data analyzer 110 stores the information from trend analyzer 154A in memory 156A, and on request from a clinician generates messages indicative of the condition of the patient. As in FIG. 7A, this information may also be transmitted to a station 114 and shown on display 116.

Figure 8A:
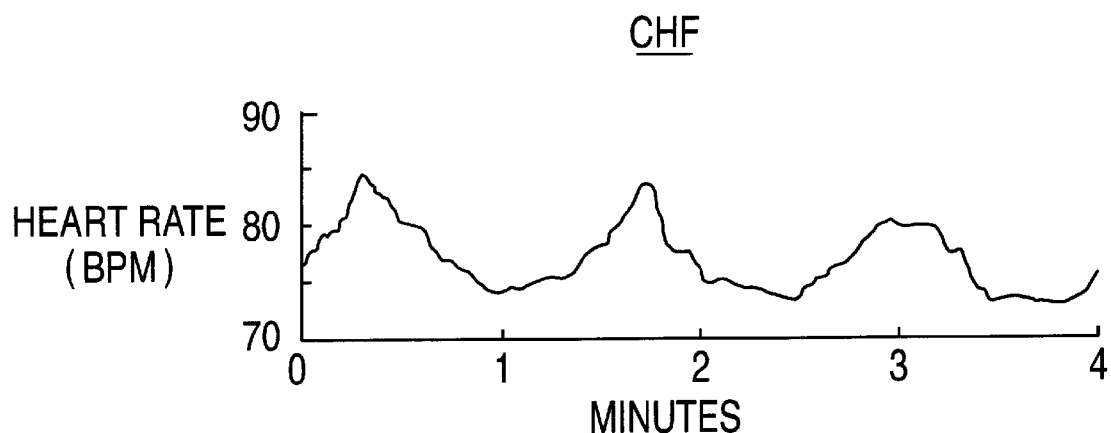
FIGS. 8A and 8B show the time domain heart rate and respiration rate of a patient with CHF.
Figure 8B:
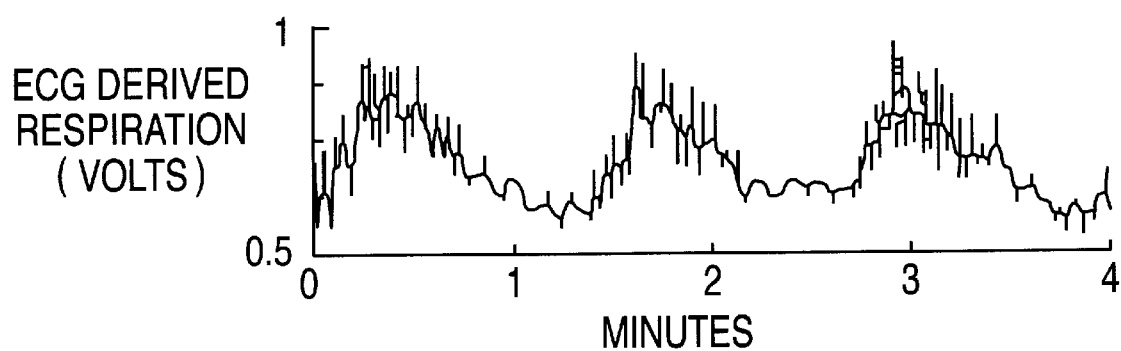
Figure 8C:
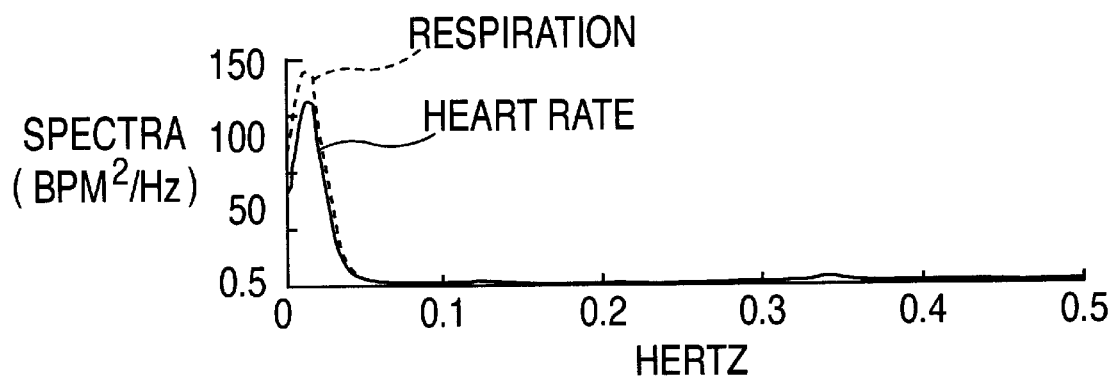
FIG. 8C shows the frequency domain heart rate and respiration rate for a person with CHF.
Figure 9A:
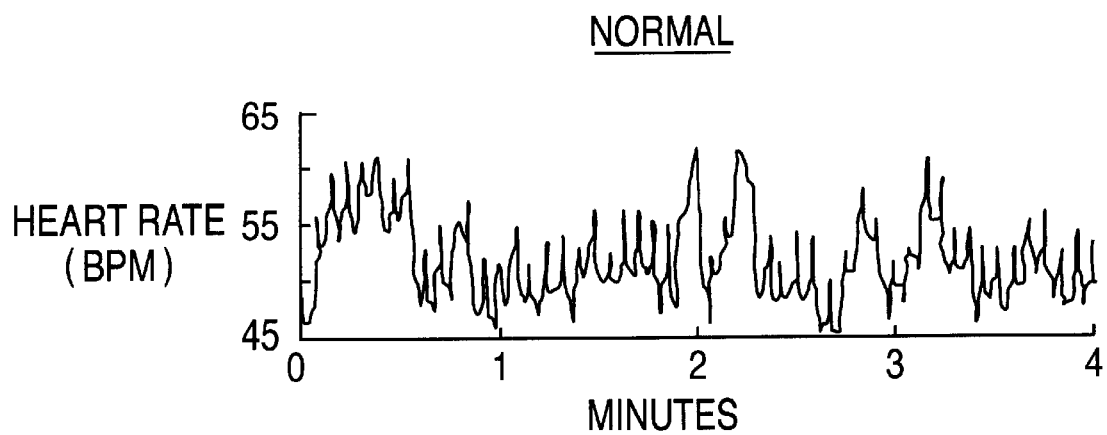
FIGS. 9A and 9B show the time domain heart rate and respiration rate for a healthy person.
Figure 9B:
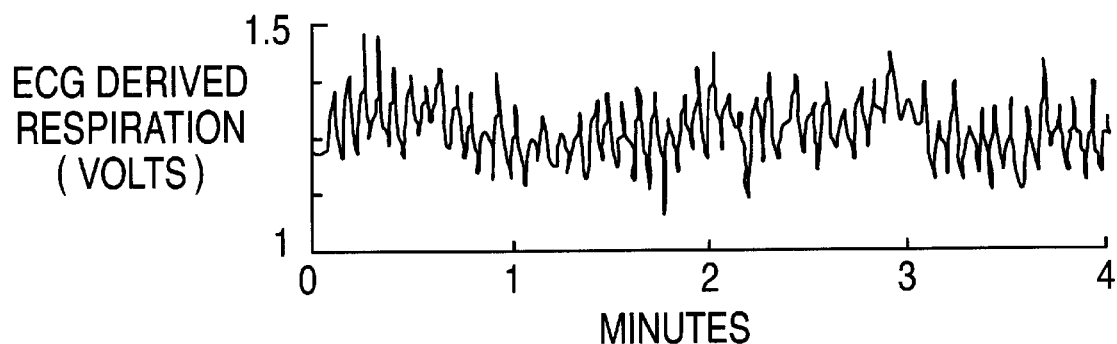
Figure 9C:
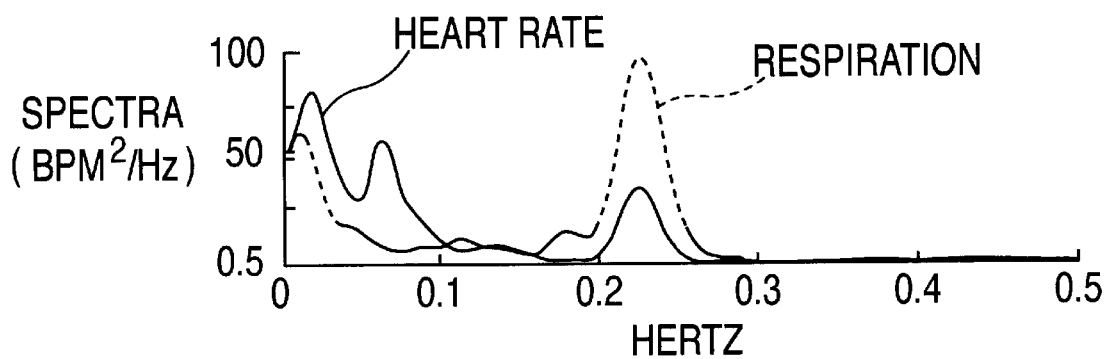
FIG. 9C shows the frequency domain heart rate and respiration rate for a healthy person.

It has been known that there is a correlation between the respiration rate variability of a cardiac patient and the progression of the patient's heart condition. This correlation is illustrated in FIGS. 8A–8C, 9A–9C and 10A–10B. FIGS. 8A and 9A show typical heart rates in the time domain for a patient with cardiac deficiency and a healthy person, respectively, and FIGS. 8B and 9B show similar respiration signals in the time domain. While the correlation may not be very clear in these figures, it is much more apparent in FIGS. 8C and 9C which show both the respiration and the heart rate in the frequency domain. As described in detail below, in the present invention various parameters associated with the patient's respiration are monitored. The long term variations of these parameters are determined by the trend analyzer of FIG. 7A or 7B.

Figure 12:
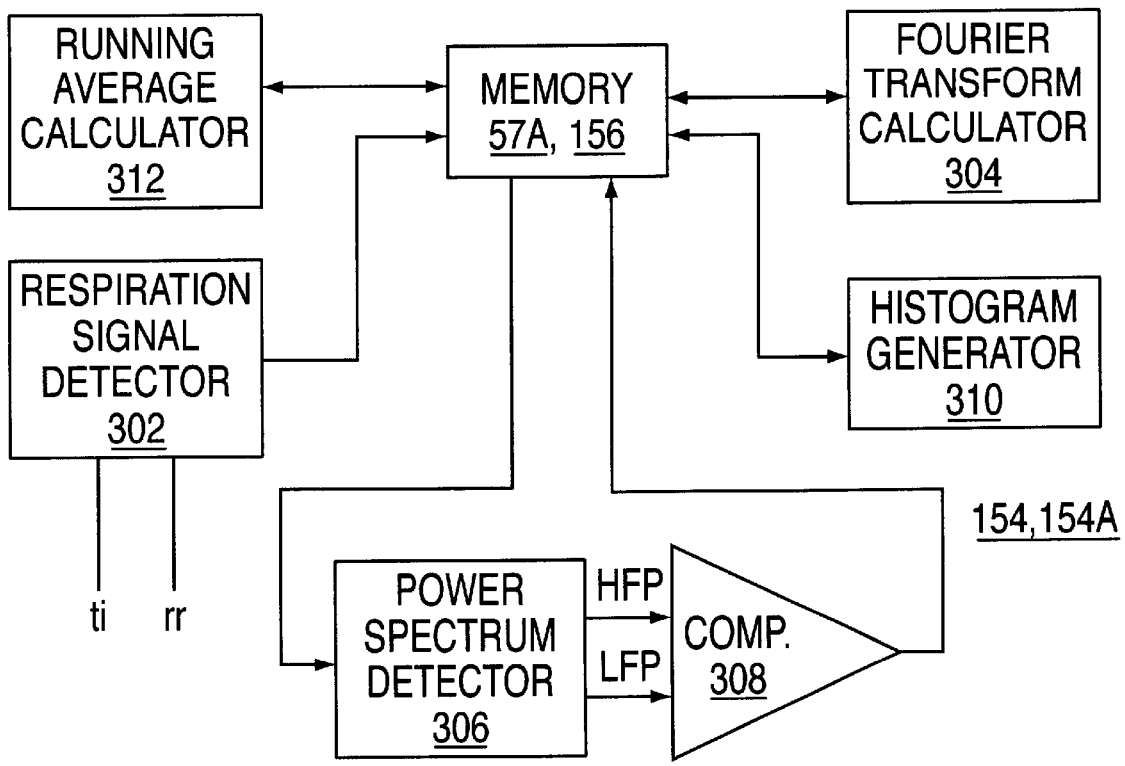
FIG. 12 shows a block diagram for a device providing a CHF determination based on respiration variability.

The respiration of a patient and its long term variability may be monitored and analyzed in a number of different ways as described in the following embodiments. In FIG. 12, the trend calculator of FIG. 7A or 7B includes a respiration detector 302 which receives samples of the transthoracic impedance signal ti. The trend calculator further includes Fourier transform calculator 304 which calculates the Fourier transform of the respiration signals stored in memory 57 or 156A generates corresponding respiration signals in the frequency domain. The trend calculator further includes a power spectrum detector 306 which detects the power content of respiration signals within predetermined frequency ranges. The output from the power spectrum detector 306 is fed to a comparator 308. The comparator 308 compares the power spectrum of frequency signals in different ranges. A histogram generator 310 is used to generate trend and histogram information descriptive of the variability of the respiration over time as indicated by the output from comparator 308. Finally, a running average calculator 312 is used to calculate a running average of a predetermined parameter indicative of respiration variability. The operation of this embodiment is now described in conjunction with FIG. 13.

Figure 10:
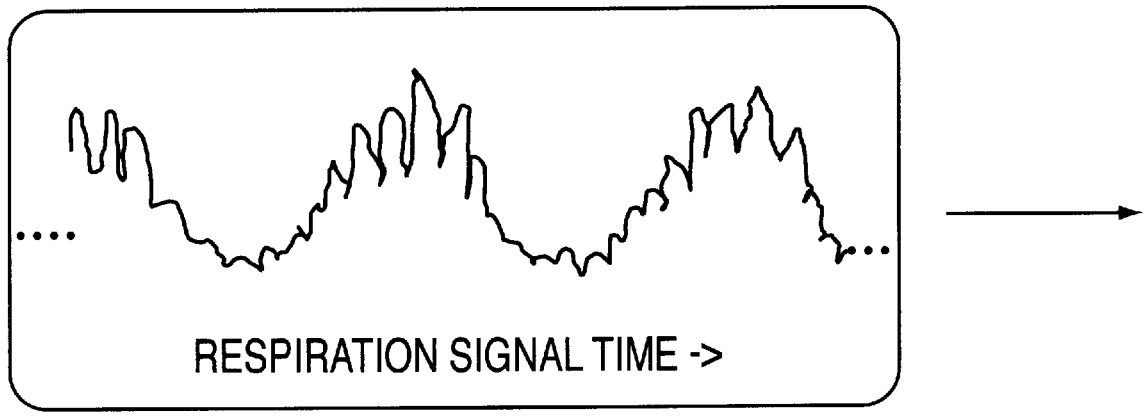
FIG. 10 shows details of a typical respiration signal as a function of time.
Figure 11:
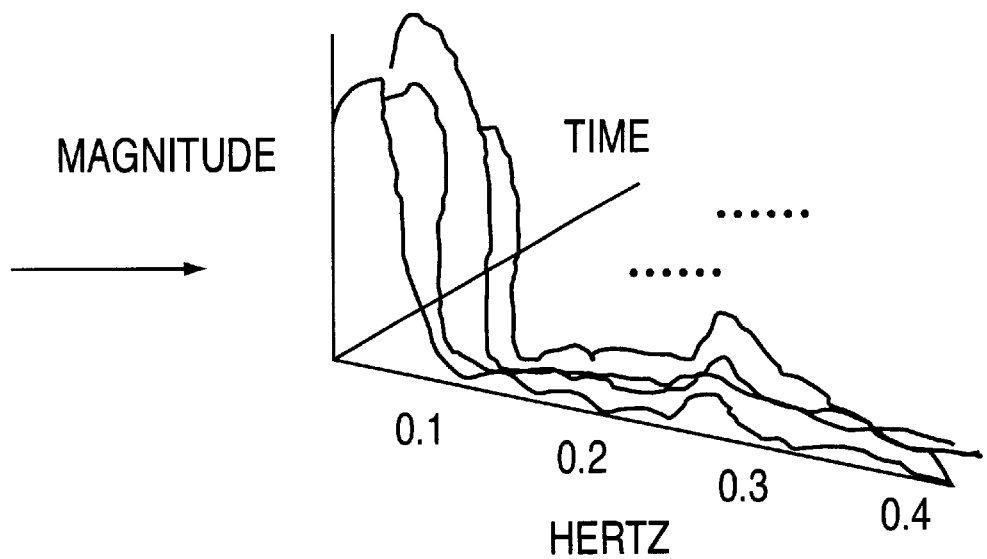
FIG. 11 shows a three dimensional representation of a respiration signal as a function of time and frequency.

Starting in step 320, the impedance signal ti indicative of the respiration of the patient is detected and recorded. For example, samples of the signal ti may be recorded every hour. In step 322 the recorded samples of the respiration signal in the time domain are transformed into corresponding samples in the frequency domain. This step is performed by the Fourier transform calculator 304. The resulting samples in the frequency domain are stored in the memory 57A, 156. FIG. 10 shows a typical respiration signal for a patient with CHF in the time domain and FIG. 11 shows several respiration signals in the frequency domain and how these respiration signals may vary over a prolonged time period.

Next, in step 324, power spectrum analyzer 306 measures the power content of the respiration signal at various frequencies over a predetermined time period, for example, three minutes. For example, the analyzer 306 may determine the power spectrum of signals above a frequency of 0.15 Hz (HFP) and signals below 0.10 Hz (LFP). The two results HFP and LFP are fed to the comparator 308 (FIG. 12) which compares the power content of the respiration signal at different frequencies. For instance, the comparator 308 may compare the relative signal power of signals having a frequency less than 0.10 Hz with signals having frequencies exceeding 0.15 Hz. As previously discussed, the signals of lower frequencies are more prevalent in cardiac patients exhibiting CHF. This comparison can be performed for each sample stored in the memory. In step 328, the trend and histogram generator 310 generates a histogram or other data indicative of the trend in the respiration variability of the patient. The histograms thus generated are stored in the memory. Also in step 328 a running average of a frequency ratio is determined and stored. The frequency ratio is defined herein as the ratio (LFP/HFP) between the power content of low to high frequency respiration signals. The running average of this ratio is calculated by the running average calculator 312. In this embodiment, this running average represents the respiration variability. All the parameters from the power spectrum detector, the comparator 308 and the running average calculator 312 are stored in memory 57A or 156.

The clinician can request to see these parameters, which can then be shown on the display 112.

At predetermined intervals, or at a clinician's request, in step 330, the respiration variation as determined by running average calculator 312 is checked to determine if the running average of the ratio has been decreasing over time. If so, in step 334 a message is displayed to a clinician such as 'BASED UPON RESPIRATION VARIABILITY, PATIENT'S CHF STATUS HAS IMPROVED'.

In step 332, a check is performed to determine if the ratio has been increasing. If so, then in step 336 another message is displayed, such as: 'BASED UPON RESPIRATION VARIABILITY, PATIENT'S CHF STATUS HAS WORSENED'.

If the ratio does not change appreciably, the following message is displayed in step 338: 'BASED UPON RESPI-

RATION VARIABILITY, PATIENT'S CHF STATUS HAS REMAINED THE SAME.'

Figure 14:
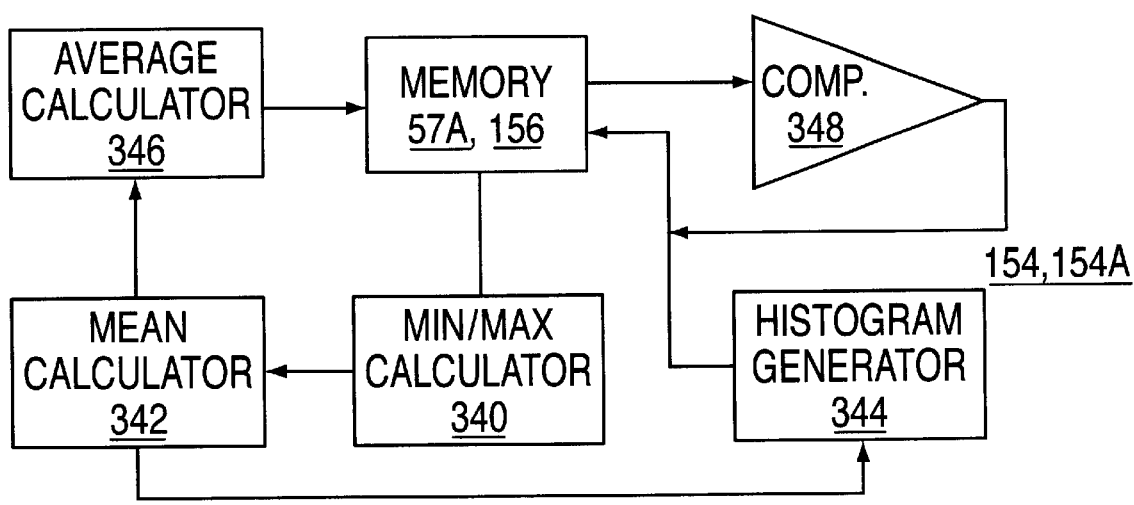
FIG. 14 shows a block diagram for a device providing CHF determination based on tidal volume.

In accordance with a second embodiment of the invention, a somewhat indirect means of determining the presence of low frequency variation in the respiration signal is made based on a low-pass filtered tidal volume. As shown in FIG. 14 for this embodiment, the trend calculator 154 (or 154A) is provided which includes a min/max calculator 340, a mean calculator 342, a histogram generator 344, an average calculator 346 and a comparator 348.

Figure 15A:
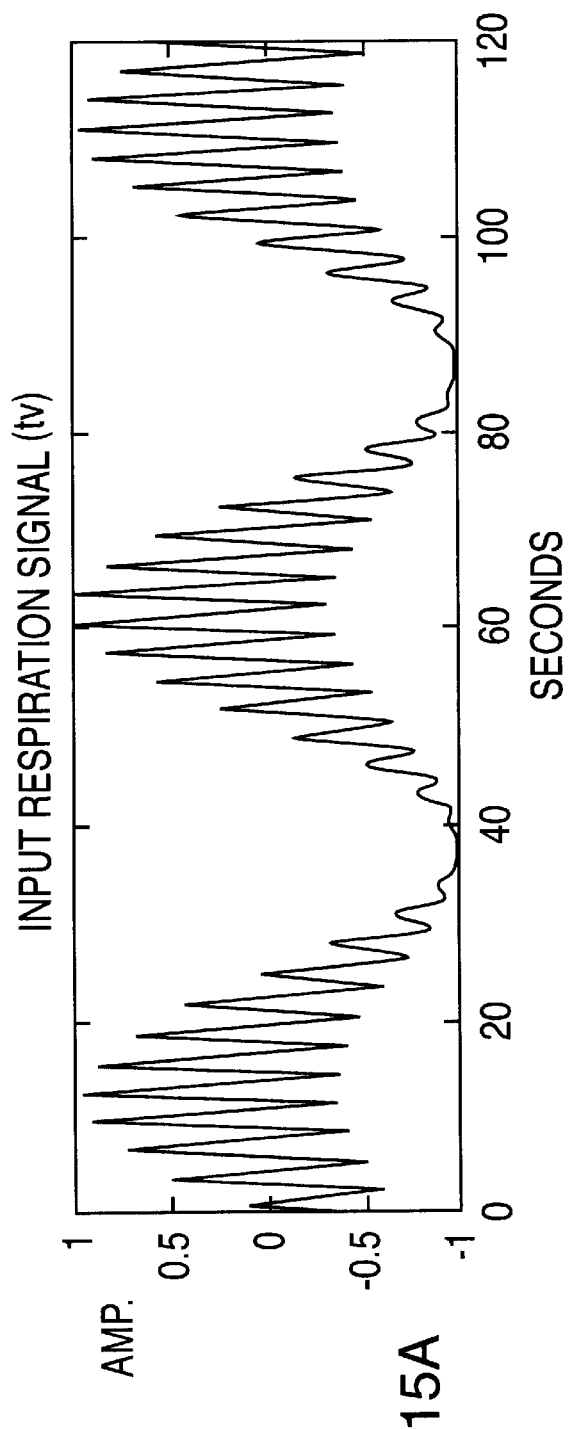
FIGS. 15A and 15B show a time dependent tidal volume and the corresponding mean value of tidal volume.
Figure 15B:
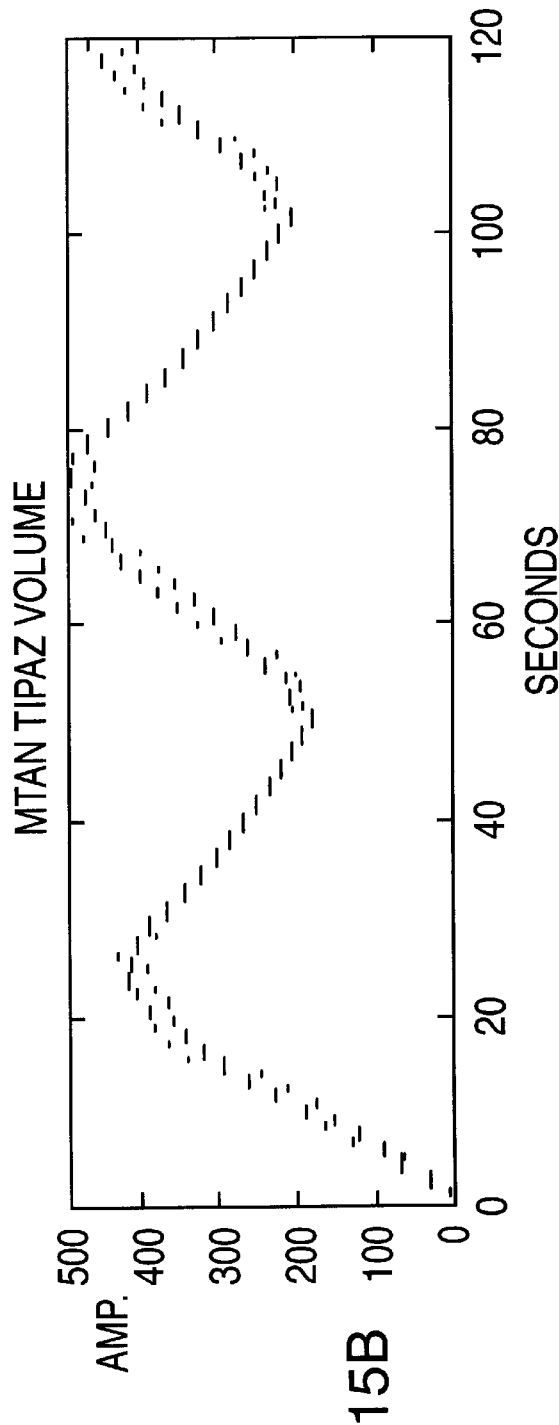

This embodiment takes advantage of the fact that the tidal volume corresponding to the respiration signal varies cyclically as shown in FIG. 15A. By filtering the respiration signal, a mean tidal volume signal is obtained as shown in FIG. 15B. This signal is indicative of the variability of the tidal volume, and correspondingly, the low frequency respiration variability.

Figure 16:
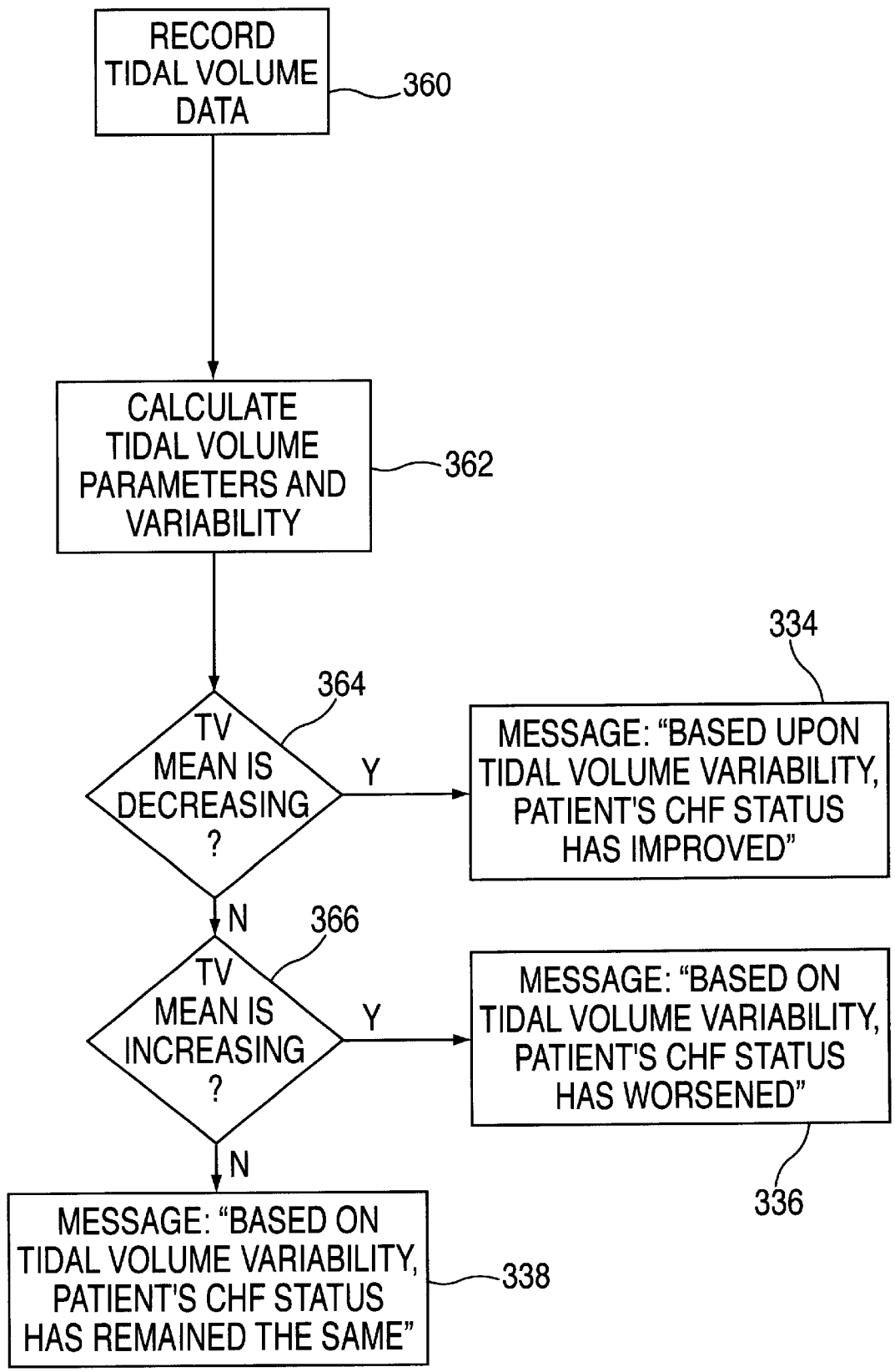
FIG. 16 shows a flow chart for the operation of the device of FIG. 14.

The determination of respiration variability using the embodiment of FIG. 14 is now described in conjunction with the flow chart shown in FIG. 16. In step 360, the tidal volume tv is received and recorded in memory 57A, 156. In step 362 the tidal volume variability is determined. More particularly, the min/max calculator 340 is used to calculate the parameters tvmin, tvmax, where tvmax is the maximum value of tv and tvmin is the minimum value of the tidal volume over a predetermined time period. These parameters are stored in the memory 57A, 156 and are also provided to tvmean calculator 342. This tvmean calculator 342 determines the tvmean parameter by taking the difference between each tvmax and corresponding tvmin parameter. The tvmean parameter is also stored in the memory.

The change in the mean value of tv over an extended time period is indicative of the tidal volume variability which is directly related to the respiration variability. The histogram generator 344 is used to monitor the parameter tvmean and to generate histograms for this parameter. In addition, the average calculator 346 may be used to generate a running average of the tvmean. This running average of tvmean in this embodiment is used to indicate the respiration variability. Both the running average of tvmean and the histograms are indicative of a trend of tvmean and are stored in the memory 57, 156A.

At predetermined intervals, or in response to a clinician's request in step 364, the comparator 348 determines if the parameter tvmean, as indicated by the histograms and/or its long term average, has been decreasing. If so, then in step 366 a message is displayed, such as: 'BASED UPON TIDAL VOLUME VARIABILITY, CHF STATUS HAS IMPROVED.' If the variability of the tidal volume has been increasing as determined in step 368, then in step 370 another message is displayed, such as: 'BASED UPON TIDAL VOLUME VARIABILITY, CHF STATUS HAS WORSENED.' If the variability remains substantially unchanged, the following message is displayed: 'BASED UPON TIDAL VOLUME VARIABILITY, CHF STATUS HAS REMAINED THE SAME' is displayed.

Figure 13:
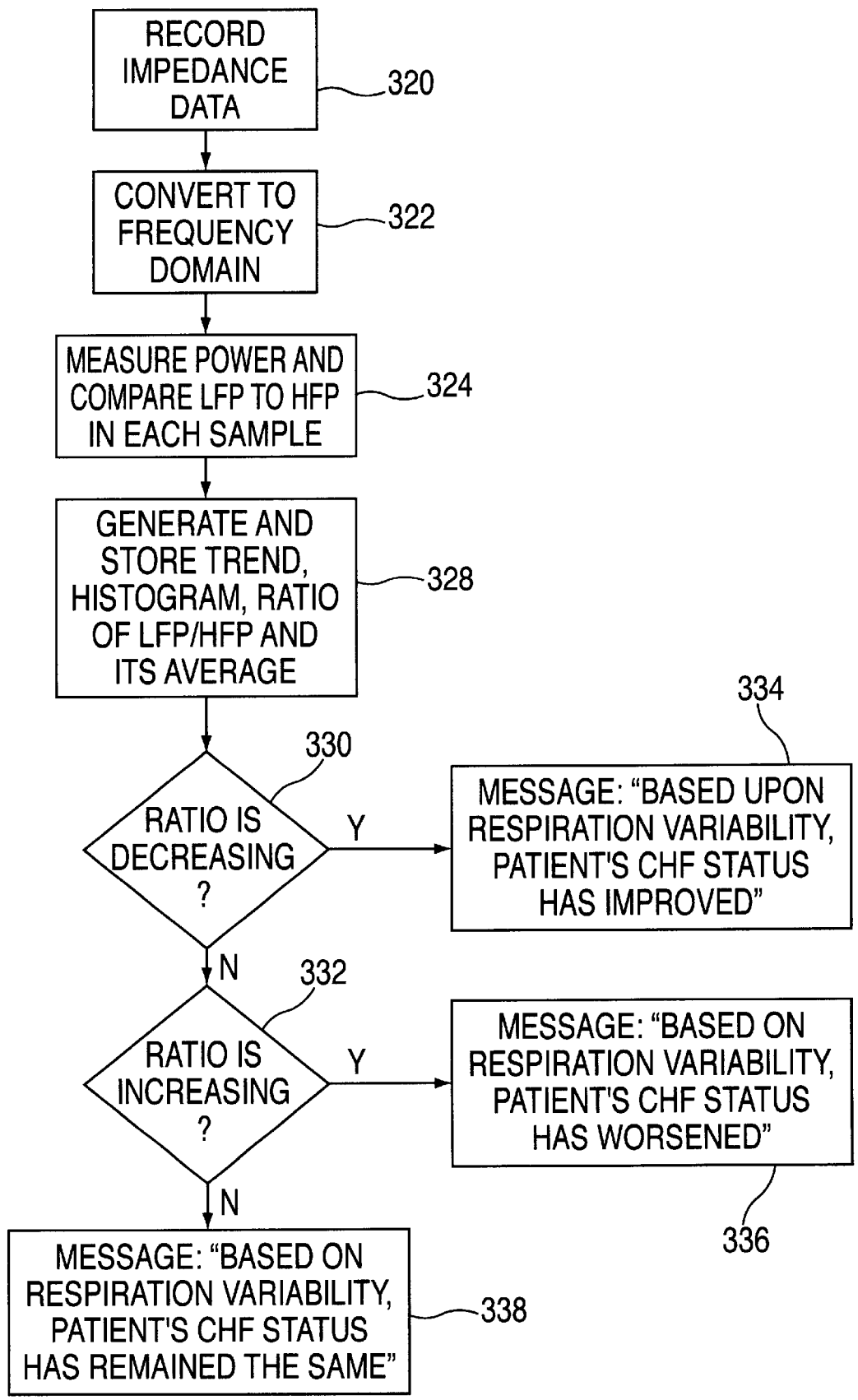
FIG. 13 shows a flow chart for the operation of the device of FIG. 12.
Figure 17:
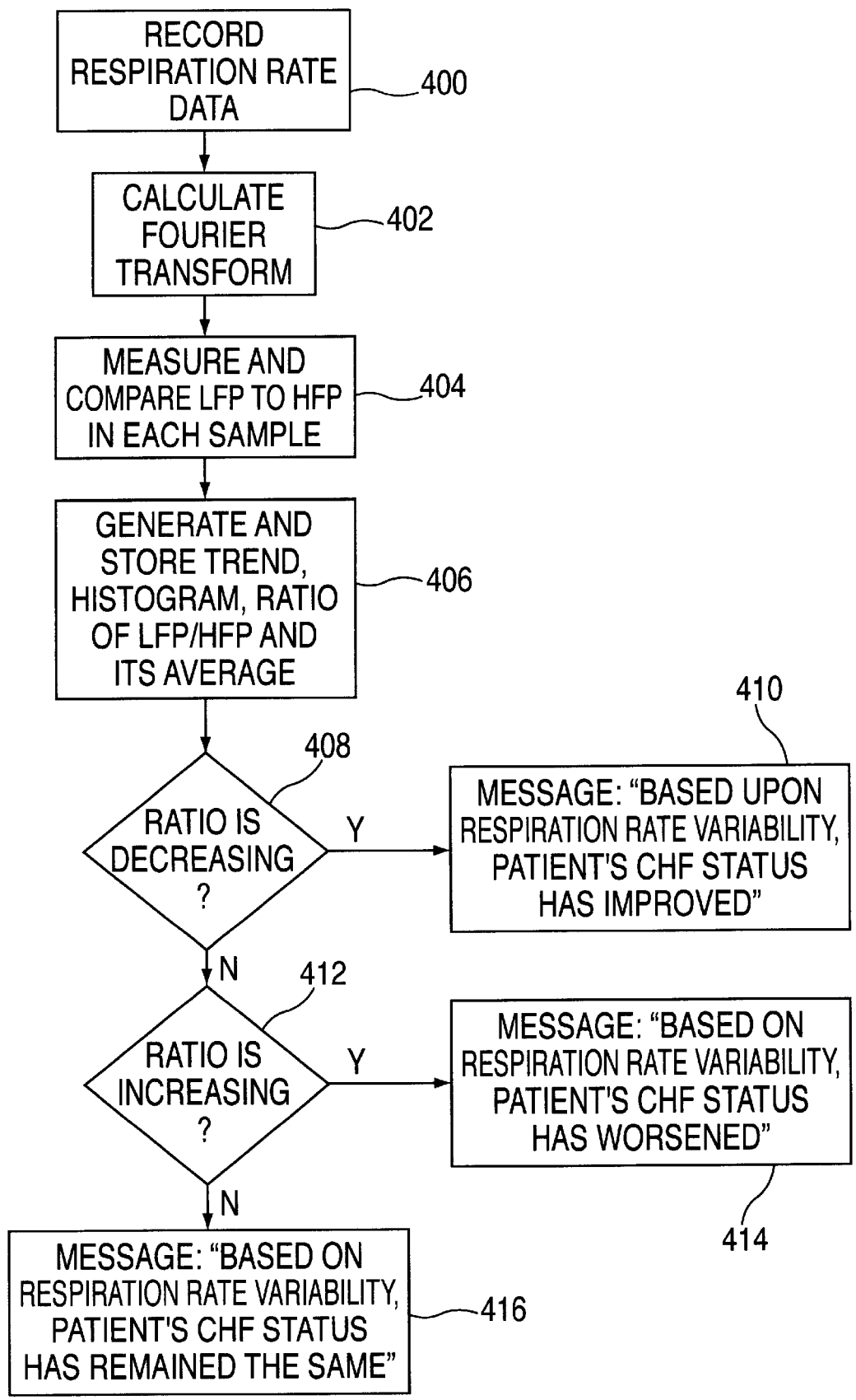
FIG. 17 shows a flow chart for CHF determination using respiration rate.
Figure 18A:
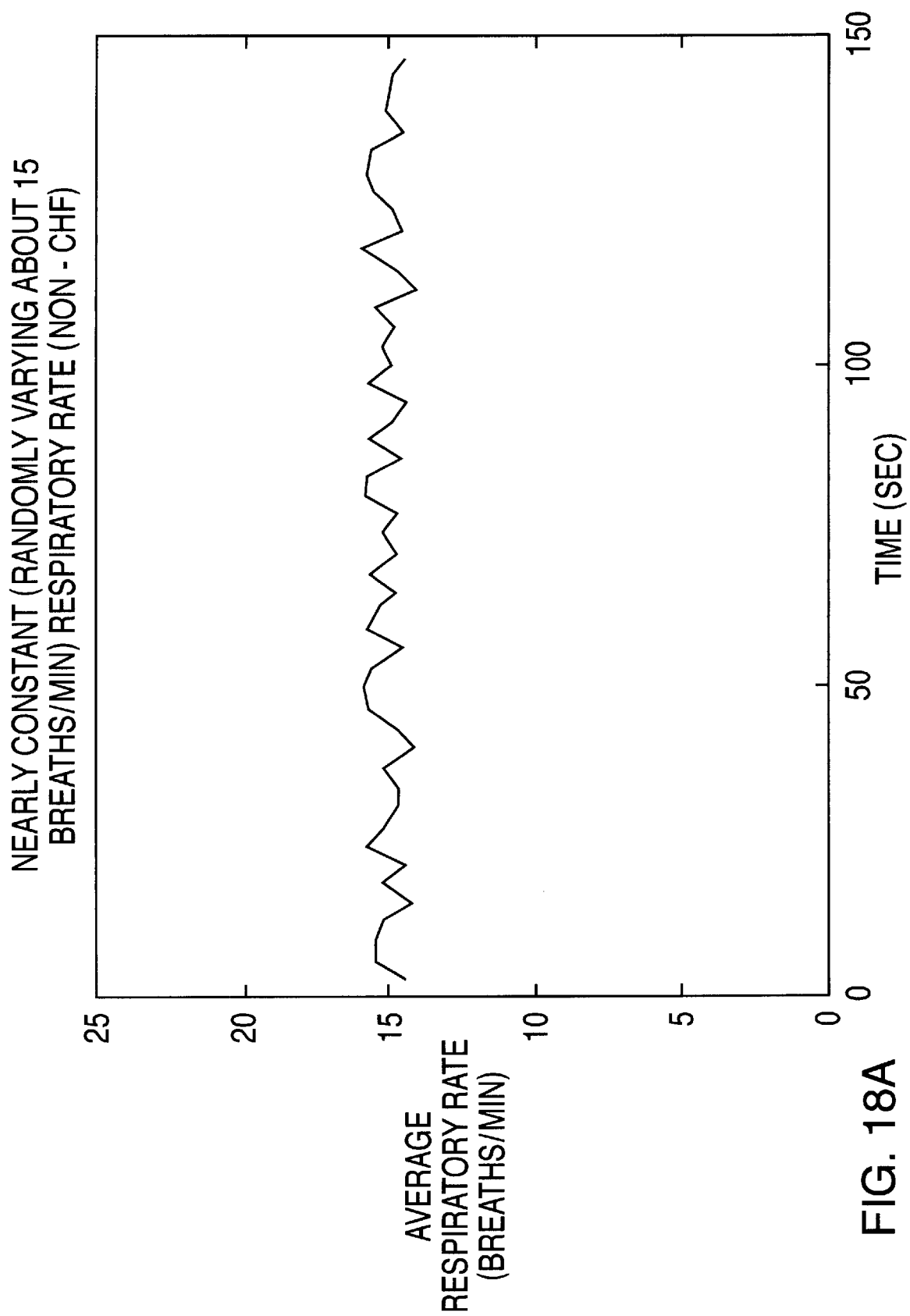
FIGS. 18A and 18B show a respiration signal for a normal person in the time and frequency domain, respectively.

In the embodiment of FIGS. 12 and 13 the respiration signal itself is analyzed to determine the respiration variability. In the embodiment of FIG. 17, instead of the respiration signal, the respiration rate is used for the same purpose. As shown in FIG. 18A, in a healthy person, the breathing rate is relatively constant, for example, about 15±1 breaths/minute. In the frequency domain shown in FIG. 18B, except for a large DC offset, the breathing rate is spread relatively evenly across the spectrum with no peaks or large excursions.

Figure 18B:
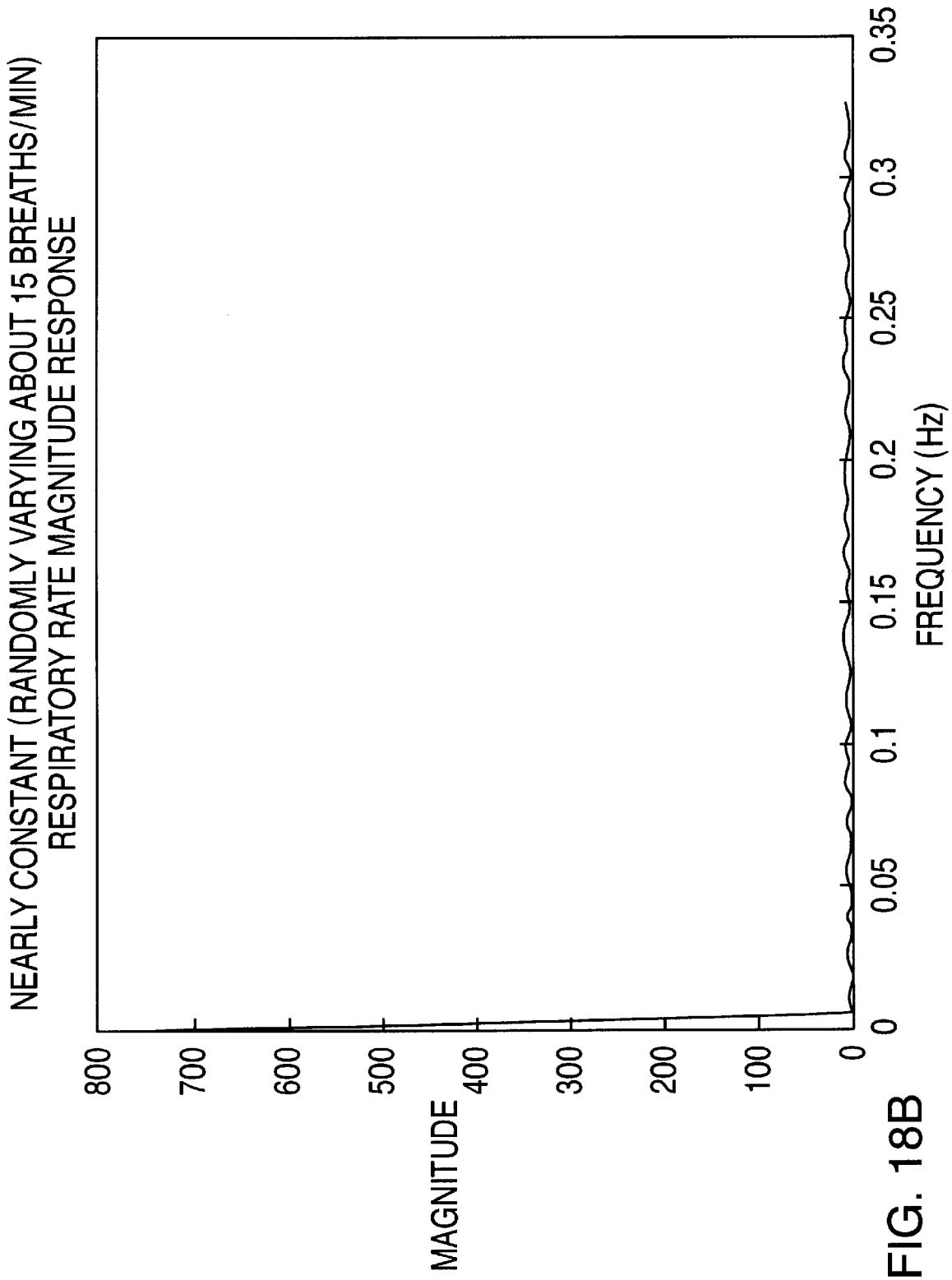
Figure 18C:
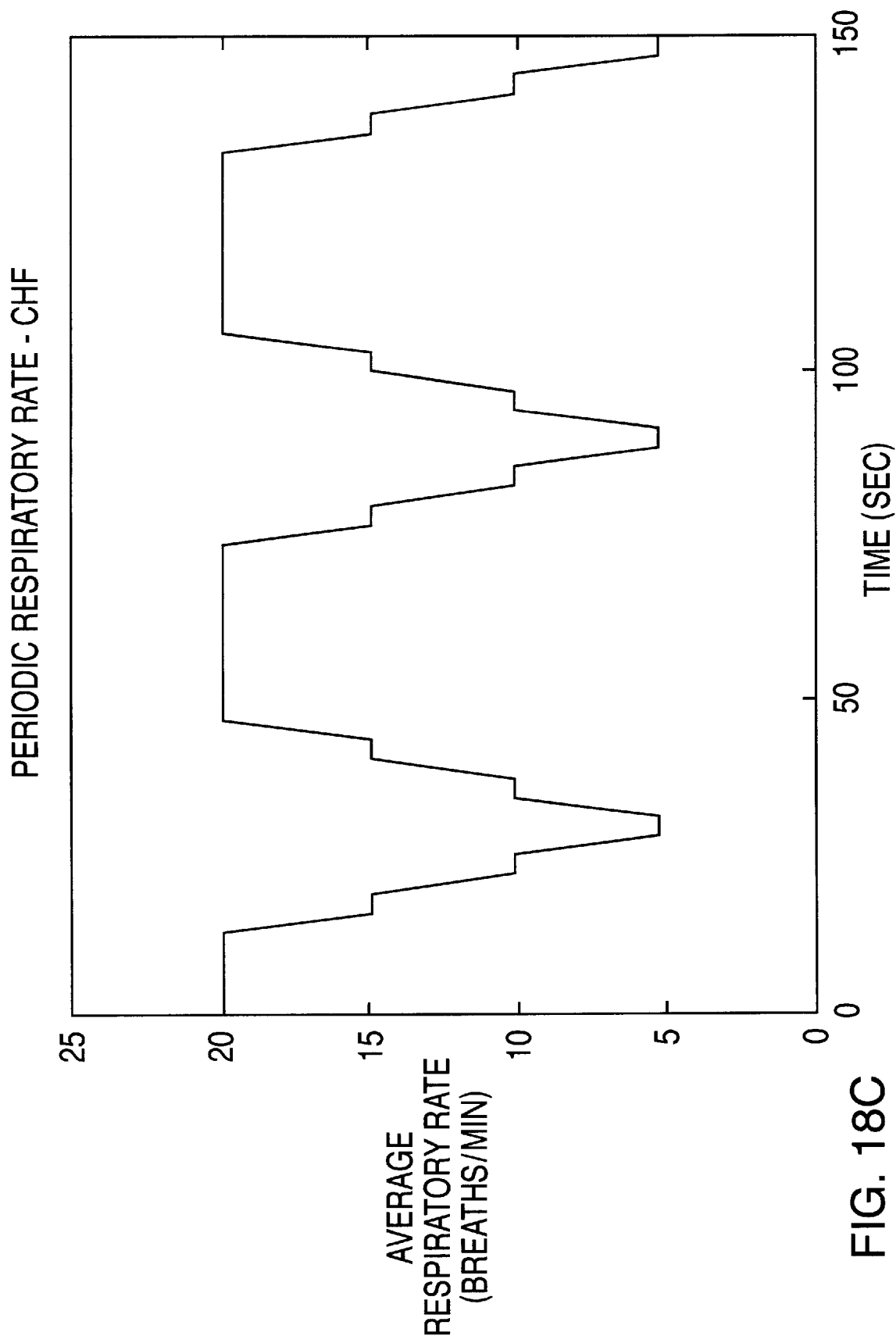
FIGS. 18C and 18D show a respiration signal for a person with CHF in the time and frequency domain, respectively.
Figure 18D:
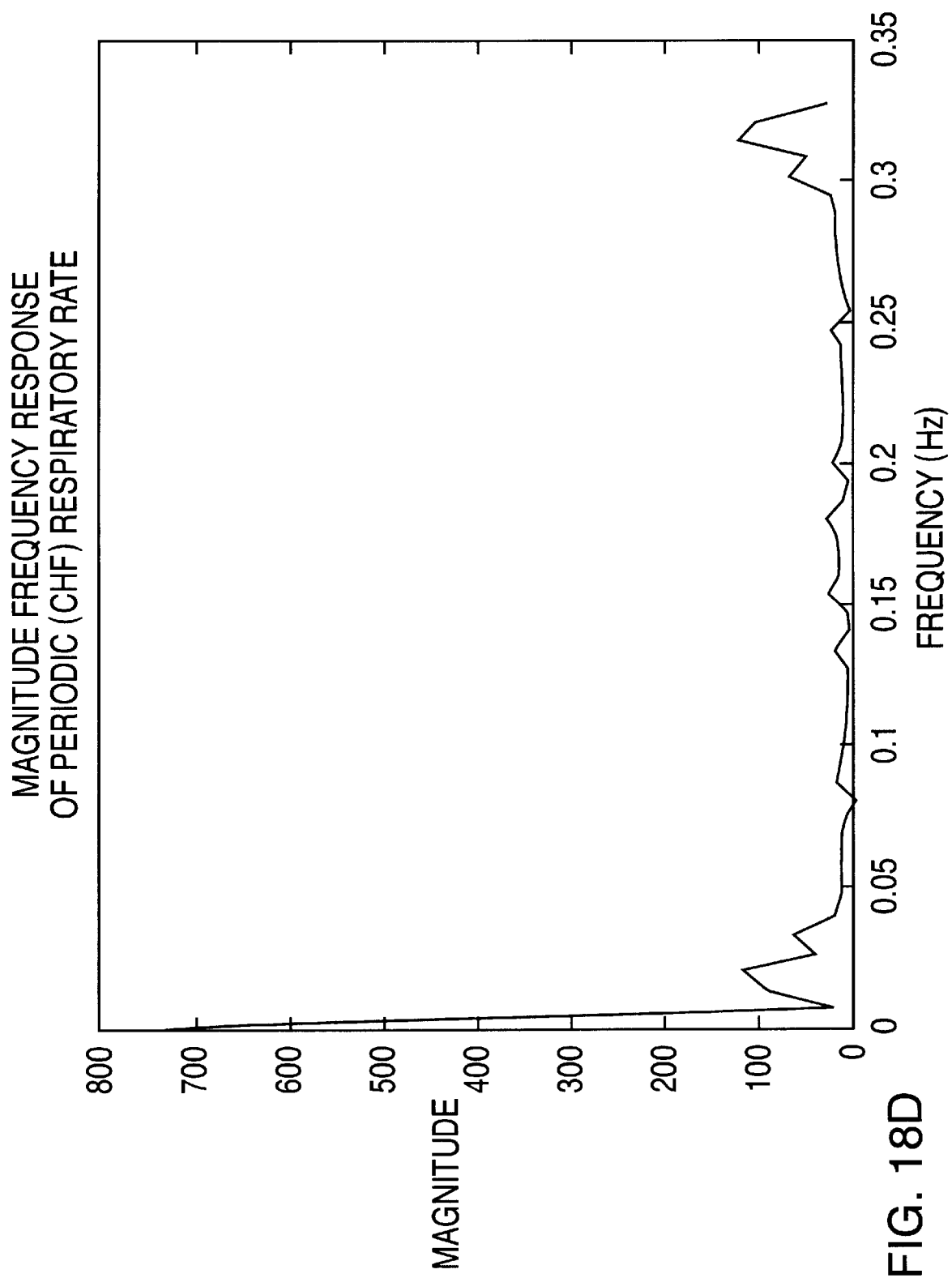

However, the respiration rate of a cardiac patient with CHF shown in FIG. 18C in the time domain and FIG. 18D in the frequency domain, varies over a much broader frequency ranging, for example, from 5 to 20 breaths/minute. In the frequency domain, this pattern has several pronounced peaks especially in the range of 0–0.05 Hz.

This phenomenon is used in a third embodiment by the same elements as in the first embodiment of FIG. 12 in accordance with the flow chart of FIG. 17. In step 400, the respiration rate signal rr is obtained and recorded into the memory (156A, 57). In step 402, the Fourier transform calculator 304 calculates the Fourier transform of the rr signal and stores the same into the memory. The Fourier transform indicates the respiration rate in the frequency domain as illustrated in FIGS. 18B and 18D. In step 404, the power spectrums at high and low frequencies (HFP and LFP) are determined as discussed above, by power spectrum detector 306. In this embodiment the ratio of the power spectrums is stored and analyzed as an indication of the respiration rate variability. In step 406, the running average calculator 312 is used to generate a long term average of the ratio. This average is stored in memory and used to generate a histogram or other parameters indicating a trend in the variability of the respiration rate.

At predetermined regular intervals, or in response to a clinician's request, in step 408 a determination is made as to whether the ratio has been decreasing over time. If so, then in step 410 the following message is generated: 'BASED UPON RESPIRATION RATE VARIABILITY PATIENT'S CHF STATUS HAS IMPROVED'.

In step 412, a determination is made as to whether the ratio has increasing over time. If so, then another message is displayed, such as: 'BASED UPON RESPIRATION RATE VARIBILITY PATIENT'S CHF STATUS HAS WORSENED'.

If the power ratio has remained substantially constant then in step 416 the following message is displayed: 'BASED UPON RESPIRATION RATE VARIABILITY PATIENT'S CHF STATUS HAS REMAINED THE SAME'

The embodiments described above are just a few of the many processes that may be used to classify and stratify the condition of a CHF patient using breathing as the criterion.

Although the invention was described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. A cardiac monitoring apparatus that monitors the cardiac condition of a patient comprising:
   a respiration sensor adapted to sense the respiration of the patient and generating corresponding respiration signal;
   an analyzer that analyzes said respiration signals to determine a long term behavior of said respiration signals, and generates a respiration variability signal when said behavior conforms to predetermined criteria indicative of the respiration variability; and
   an output device receiving said respiration variability signal and generating an output signal based on said respiration variability signal and indicative of a congestive heart failure status of said patient.

2. The apparatus of claim 1 further comprising an implantable cardiac device arranged and constructed to generate cardiac stimulation signals for the patient's heart wherein said respiration sensor is disposed inside said implantable cardiac device and said analyzer is disposed at a location remote from the patient, said apparatus further comprising a communication channel for transmitting said respiration signals to said analyzer.

3. The apparatus of claim 1 wherein said respiration sensor and at least a portion of said analyzer are disposed in said device and said output device is disposed at a remote location.

4. The apparatus of claim 1 wherein said analyzer includes a memory storing said respiration signals over a predetermined time period, a calculator determining said respiration variability signal, wherein said analyzer is adapted to evaluate a trend of said variability over an extended time period.

5. A cardiac monitoring apparatus that monitors the cardiac condition of a patient comprising:
   a respiration sensor adapted to sense the respiration of the patient and generating corresponding respiration signal;
   an analyzer that analyzes said respiration signals to determine a long term behavior of said respiration signals, and generates a respiration variability signal when said behavior conforms to predetermined criteria indicative of the respiration variability; and
   an output device receiving said respiration variability signal and generating an output signal based on said respiration variability signal indicative of a cardiac condition of said patient;
   wherein said analyzer includes a frequency detector that detects and analyzes the frequency of said respiration signals and a power calculator for calculating the power levels above and below a cutoff frequency.

6. The apparatus of claim 5 wherein said frequency detector further comprises a comparator that compares a ratio of the power levels of high and low frequency signal components, said ratio being indicative of said respiration variability signal.

7. The apparatus of claim 6 wherein said analyzer further comprises a trend detector coupled to said comparator and arranged to detect a trend in said ratio, and wherein said respiration variability signal corresponds to said trend.

8. The apparatus of claim 7 wherein said output device generates a first output signal if said respiration variability signal indicates that said ratio has been decreasing over time and a second output signal if said respiration variability signal indicates that said ratio has been increasing over time.

9. The apparatus of claim 1 wherein said respiration sensor includes an impedance detector that detects and measures a transthoracic impedance of the patient as a function of respiration.

10. A cardiac monitoring apparatus that monitors the cardiac condition of a patient comprising:
    a respiration sensor adapted to sense the respiration of the patient and generating corresponding respiration signal;
    an analyzer that analyzes said respiration signals to determine a long term behavior of said respiration signals, and generates a respiration variability signal when said behavior conforms to predetermined criteria indicative of the respiration variability; and
    an output device receiving said respiration variability signal and generating an output signal based on said respiration variability signal indicative of a cardiac condition of said patient;
    wherein said respiration sensor includes a tidal volume detector that detects and measures a tidal volume of the patient and a calculator that calculates said respiration signal from said tidal volume.

11. The apparatus of claim 1 wherein said respiration sensor includes a respiration rate calculator that calculates a respiration rate for the patient and wherein said analyzer is adapted to analyze said respiration rate to determine said congestive heart failure status of the patient.

12. A cardiac monitoring apparatus for a patient comprising:
    a respiration sensor that senses a breathing pattern of the patient and generates a corresponding respiration signal;
    an analyzer that receives said respiration signal and analyzes said signal to determine if said breathing pattern corresponds to preselected criteria, said analyzer generating an indication signal; and
    an output device coupled to said analyzer that receives said indication signal, said output device generating an output corresponding to said indication signal, said output corresponding to a congestive heart failure (CHF) status.

13. The apparatus of claim 12 wherein said respiration sensor includes an impedance detector that detects a transthoracic impedance of the patient and a calculator that calculates said respiration signal from said transthoracic impedance.

14. The apparatus of claim 12 wherein said respiration sensor includes a tidal volume detector that detects a tidal volume of the patient and a calculator that calculates a respiration signal based on said tidal volume.

15. The apparatus of claim 12 wherein said analyzer calculates a rate of respiration of the patient from said respiration signal.

16. The apparatus of claim 15 wherein said analyzer includes a variability detector that receives said rate and calculates a variability of said respiration rate.

17. The apparatus of claim 16 further comprising a trend detector that detects a trend in said variability, said trend being related to the CHF status of the patient.

18. A cardiac monitoring apparatus for a patient comprising:
    a respiration sensor that senses a breathing pattern of the patient and generates a corresponding respiration signal;
    an analyzer that receives said respiration signal and analyzes said signal to determine if said breathing pattern corresponds to preselected criteria, said analyzer including a calculator that calculates a rate of respiration of the patient from said respiration signal, an da variability detector that receives said rate and calculates a varibility of said respiration rate, said analyzer generating an indication signal indicative of the cardiac condition of the patient based on said variability; and
    an output device coupled to said analyzer that receives said indication signal, said output device generating an output corresponding to said indication signal;
    wherein said variability detector includes a power detector that detects a relative power of high respiration rate signals and a relative power of low respiration signals, said high an low respiration rate signals defined as being higher an lower than a preselected rate threshold, respectively.

19. The apparatus of claim 12 wherein said analyzer further includes a variability detector that analyzes a variability of said breathing pattern.

20. The apparatus of claim 19 wherein said analyzer generates a first indication signal if said ratio decreases over time, said first indication signal being indicative of an improved CHF status of the patient, and a second signal if said variability decreases over time, said second signal being indicative of a worsened CHF status.

21. The apparatus of claim 12 wherein said respiration monitor is implantable in the patient.

22. A method of determining the cardiac condition of a patient comprising:
    detecting a respiration signal indicative of a current respiration of the patient;
    analyzing said respiration signal to determine if said respiration signal meets predetermined criteria related to a congestive heart failure (CHF) status of the patient; and
    generating an indication signal corresponding to said CHF status and based on said analysis.

23. The method of claim 22 wherein said step of detecting said respiration signal comprises detecting a transthoracic impedance of the patient, said transthoracic impedance being dependent on said respiration signal.

24. The method of claim 22 wherein said step of analyzing includes detecting a variability of said respiration signal.

25. A method of determining the cardiac condition of a patient comprising:
    detecting a respiration signal indicative of a current respiration of the patient;
    analyzing said respiration signal to determine if said respiration signal meets predetermined criteria related to the cardiac condition of the patient; and
    generating an indication signal corresponding to said cardiac condition and based on said analysis;
    wherein said step of analyzing includes detecting a high signal power of respiration signals having a frequency above a predetermined threshold and detecting a low signal power of respiration signals having a frequency below said predetermined threshold.

26. The method of claim 25 wherein said step of analyzing further includes determining a ratio of said high signal power and low signal power.

27. The method of claim 26 wherein said step of analyzing further comprises analyzing a trend of said ratio.

28. The method of claim 27 further comprising generating a first signal indicative of improved CHF status of the patient and a second signal indicative of worsened CHF status based on said trend.

29. A cardiac monitoring apparatus for a patient comprising:
    a respiration sensor that senses a breathing pattern of the patient and generates a corresponding respiration signal;
    an analyzer that receives said respiration signal and analyzes said signal to determine if said breathing pattern corresponds to preselected criteria, calculates a rate of respiration of the patient from said respiration signal calculates a variability of said respiration rate and generates an indication signal indicative of a congestive heart failure status of the patient based on said variability; and
    an output device coupled to said analyzer that receives said indication signal, said output device generating an output corresponding to said indication signal.

30. The apparatus of claim 29 wherein said respiration sensor includes an impedance detector that detects a transthoracic impedance of the patient and a calculator that calculates said respiration signal from said transthoracic impedance.

31. The apparatus of claim 29 wherein said respiration sensor includes a tidal volume detector that detects a tidal volume of the patient and a calculator that calculates a respiration signal based on said tidal volume.

32. A method of determining a cardiac condition of a patient comprising:
    detecting a respiration signal indicative of a current respiration of the patient;
    analyzing said respiration signal including detecting a variability of said respiration signal to determine if said respiration signal meets predetermined criteria related to the congestive heart failure status of the patient; and
    generating an indication signal corresponding to said congestive heart failure status and based on said analysis.

33. The method of claim 32 wherein said step of detecting said respiration signal comprises detecting a transthoracic impedance of the patient, said transthoracic impedance being dependent on said respiration signal.

* * * * *